US012678134B2

(12) United States Patent
     Kobayashi et al.

(10) Patent No.: US 12,678,134 B2
(45) Date of Patent: Jul. 14, 2026

(54) ULTRASONIC PROBE

(71) Applicant: CANON KABUSHIKI KAISHA,
Tokyo (JP)

(72) Inventors: Yusuke Kobayashi, Nasushiobara (JP);
Hiroyuki Shikata, Nasushiobara (JP)

(73) Assignee: CANON KABUSHIKI KAISHA,
Tokyo (JP)

( * ) Notice: Subject to any disclaimer, the term of this
patent is extended or adjusted under 35
U.S.C. 154(b) by 0 days.

(21) Appl. No.: 18/930,450

(22) Filed: Oct. 29, 2024

(65) Prior Publication Data

US 2025/0143671 A1      May 8, 2025

(30) Foreign Application Priority Data

Nov. 2, 2023      (JP) .................................. 2023-188384

(51) Int. Cl.
     *A61B 8/00*          (2006.01)
(52) U.S. Cl.
     CPC ............ *A61B 8/4444* (2013.01); *A61B 8/429*
                                              (2013.01)
(58) Field of Classification Search
     CPC . A61B 8/4444; A61B 8/429; A61B 2090/064;
                    A61B 2090/065; A61B 2090/066
     See application file for complete search history.

(56) References Cited

U.S. PATENT DOCUMENTS

| | | | | |
|---|---|---|---|---|
| 2002/0103436 A1* | 8/2002 | Njemanze | ............ | A61B 8/4227 |
| | | | | 600/453 |
| 2006/0158429 A1* | 7/2006 | Harley | ................ | G06F 3/03543 |
| | | | | 345/157 |
| 2008/0081993 A1* | 4/2008 | Waki | ........................ | A61B 8/14 |
| | | | | 600/438 |

FOREIGN PATENT DOCUMENTS

| | | | | |
|---|---|---|---|---|
| JP | 2019-76298 A | 5/2019 | | |
| WO | WO-2019127117 A1 * | 7/2019 | ............... | A61B 8/00 |

* cited by examiner

*Primary Examiner* — Serkan Akar
*Assistant Examiner* — Tommy T Ly
(74) *Attorney, Agent, or Firm* — Oblon, McClelland,
Maier & Neustadt, L.L.P.

(57)          ABSTRACT

An ultrasonic probe of an embodiment includes a transmission and reception unit, a movable unit, a pressure signal detection unit, and an amplification unit. The transmission and reception unit includes a plurality of transducers, transmits transmission acoustic signals generated by the transducers, and receives reflection acoustic signals of the transmitted acoustic signals. The movable unit includes an acoustic radiation surface provided on a surface of the transmission and reception unit and moves due to a pressure applied to the acoustic radiation surface pressed against an object. The pressure signal detection unit detects a pressure signal corresponding to an amount of movement of the movable unit. The amplification unit amplifies the amount of movement of the movable unit.

11 Claims, 3 Drawing Sheets

ULTRASONIC PROBE

CROSS-REFERENCE TO RELATED APPLICATIONS

Priority is claimed on Japanese Patent Application No. 2023-188384, filed Nov. 2, 2023, the content of which is incorporated herein by reference.

BACKGROUND

Field of the Invention

An embodiment disclosed in the present specification and drawings relates to an ultrasonic probe.

Description of Related Art

An ultrasonic diagnostic device is a device that extracts an acoustic image using ultrasound transmitted and received by an acoustic transducer provided in a transmission and reception unit of an ultrasonic probe. In an ultrasonic diagnostic device, an ultrasonic probe is pressed against a subject and used. The ultrasonic diagnostic device detects a pressure when the ultrasonic probe is pressed against the subject using a pressure sensor, calculates an orientation and a position of the ultrasonic probe relative to the subject, and uses them to generate an acoustic image. In the related art, there is a technique of detecting a pressure applied to an acoustic radiation surface of a surface of an acoustic transducer inside a probe body via a transmission material and extracting a pressure signal together with an acoustic image.

SUMMARY

In the above ultrasonic probe in the related art, in order to apply a pressure to a pressure sensor, a transmission and reception unit provided with the acoustic radiation surface and the probe body provided with the pressure sensor need to move apart, and the acoustic radiation surface needs to move relative to the probe body. However, since ultrasonic probes are usually used hygienically in medical institutions, and it is thus required to eliminate a gap between the probe body and the transmission and reception unit. For this reason, if the gap between the probe body and the transmission and reception unit is filled with, for example, a sealant, it becomes difficult for the acoustic radiation surface to move, and an amount of movement of the transmission and reception unit becomes smaller. Since a pressure sensor detects, for example, pressures of up to several tens of newtons, it is necessary to interpose a spring with a relatively large spring constant between the acoustic radiation surface and the pressure sensor. For this reason, a large spring is required, and thus the entire ultrasonic probe must be made larger.

DETAILED DESCRIPTION

An ultrasonic probe according to an embodiment will be described below with reference to the drawings. The ultrasonic probe according to the embodiment includes a transmission and reception unit, a movable unit, a pressure signal detection unit, and an amplification unit. The transmission and reception unit includes a plurality of transducers, transmits transmission acoustic signals generated by the transducers, and receives reflection acoustic signals of the transmission acoustic signals. The movable unit includes an acoustic radiation surface provided on a surface of the transmission and reception unit and moves due to a pressure applied to the acoustic radiation surface pressed against an object. The pressure signal detection unit detects a pressure signal corresponding to an amount of movement of the movable unit. The amplification unit amplifies the amount of movement of the movable unit. Due to such a configuration, it is possible to inhibit enlargement of a size of the ultrasonic probe.

First Embodiment

Figure 1:
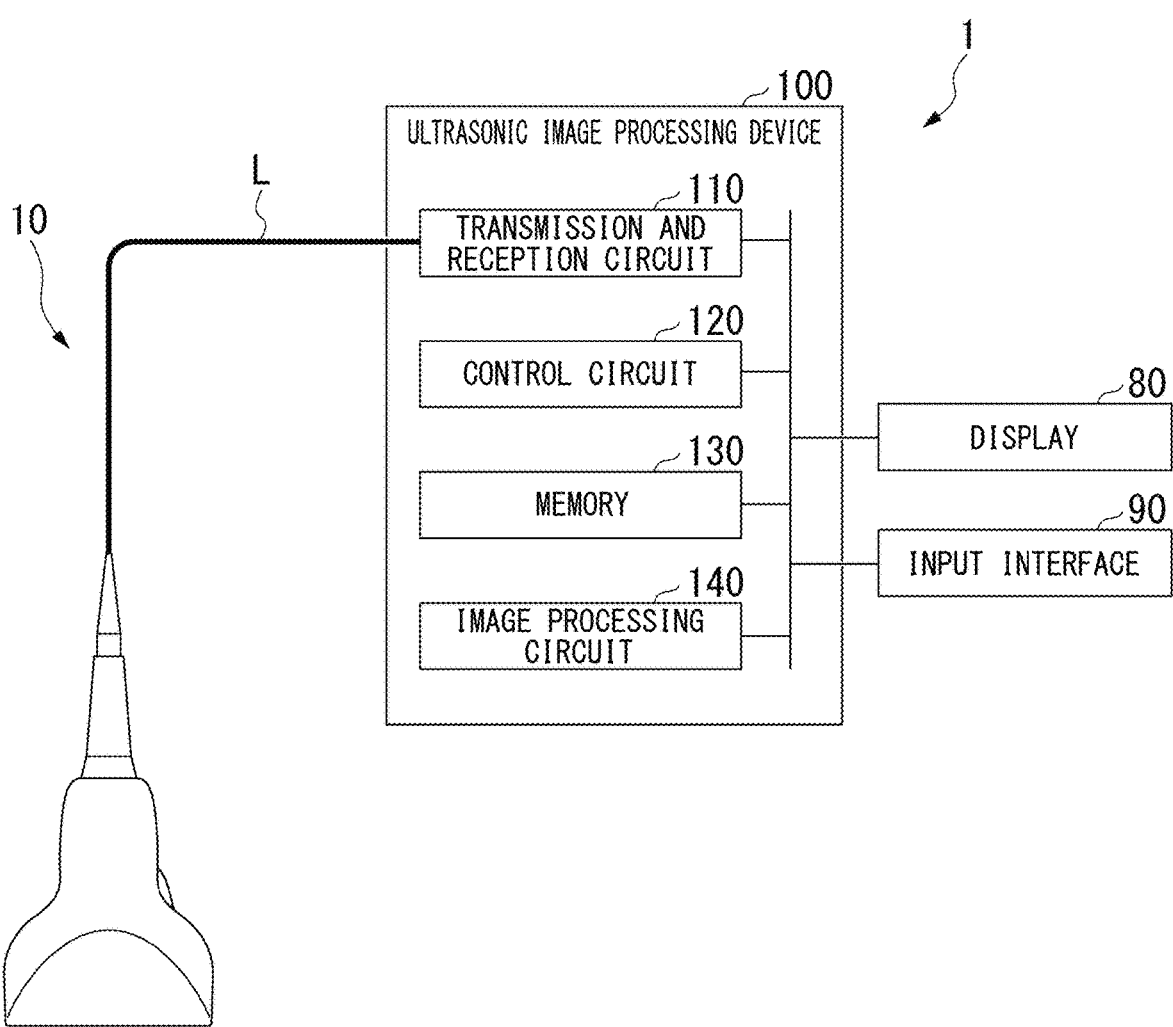
FIG. 1 is a block diagram showing an example of a configuration of an ultrasonic diagnostic device according to a first embodiment.

FIG. 1 is a block diagram showing a configuration example of an ultrasonic diagnostic device 1 according to a first embodiment. The ultrasonic diagnostic device 1 includes, for example, an ultrasonic probe 10, a display 80, an input interface 90, and an ultrasonic image processing device 100. The ultrasonic probe 10 is brought into contact with, for example, a body surface of a subject and executes transmission and reception of ultrasound to and from the subject. The ultrasonic probe 10 is connected to the ultrasonic image processing device 100 via a cable L and performs transmission and reception of signals to and from the ultrasonic image processing device 100.

Figure 2:
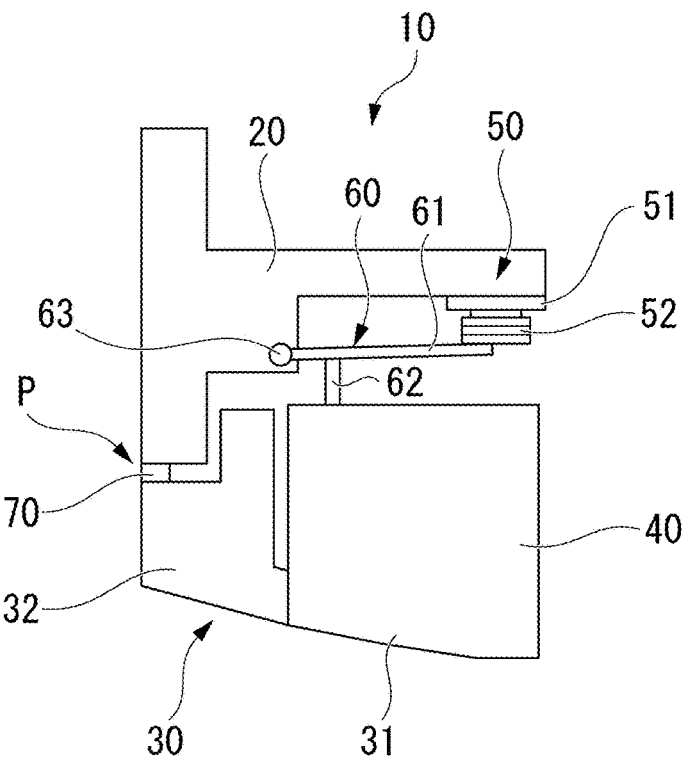
FIG. 2 is a cross-sectional view of main parts of an ultrasonic probe according to the first embodiment.

FIG. 2 is a cross-sectional view of main parts of the ultrasonic probe 10 according to the first embodiment. The ultrasonic probe 10 includes, for example, a probe body 20, a transmission and reception unit 30, a movable unit 40, a pressure signal detection unit 50, and a lever unit 60. FIG. 2 shows a cross-section near an end portion at a position of a portion of the ultrasonic probe 10 at which the probe body 20 is connected to the transmission and reception unit 30.

The probe body 20 includes a gripping portion shaped to be easily gripped by an operator, such as a doctor or technician. The probe body 20 is a portion gripped by the operator during an examination or diagnosis. The gripping portion of the probe body 20 is a portion gripped by the operator who uses the ultrasonic probe 10, for example. The probe body 20 is made of, for example, a resin.

The probe body 20 has a vertically elongated shape with the gripping portion at its center. The transmission and reception unit 30 is attached to a tip of the probe body 20. The operator holds the ultrasonic probe 10 by gripping the gripping portion of the probe body 20 and performs an examination or the like while pressing the transmission and reception unit 30 against, for example, an examination target position of the subject.

An acoustic radiation surface 31 is provided on a surface of the transmission and reception unit 30. The acoustic radiation surface 31 of the transmission and reception unit 30 moves relative to the probe body 20 when an object, for example, an examination portion in a body of the subject, is pressed against it. The transmission and reception unit 30 includes a plurality of transducers. The transducers are electrically independent from each other. The transmission and reception unit 30 transmits transmission acoustic signals generated by the transducers and receives reflection acoustic signals of the transmission acoustic signals. The plurality of transducers can be driven individually.

The transducers are arranged, for example, by dicing a base material of the transmission and reception unit 30. The transmission and reception unit 30 vibrates the transducers and generates ultrasound serving as the transmission acoustic signals on the basis of drive signals (electrical signals) supplied by the ultrasonic image processing device 100.

The transmission acoustic signals generated by the vibrations of the transducers are reflected by an acoustic impedance mismatch surface in the subject and become reflected waves. The reflected waves are received by the transducers as the reflection acoustic signals (electrical signals) that include components scattered by scatterers in the tissue. The ultrasonic probe 10 transmits the received reflection acoustic signals to the ultrasonic image processing device 100.

The transmission and reception unit 30 is attached to the movable unit 40. The movable unit 40 moves due to a pressure applied to the acoustic radiation surface 31 pressed against an object such as the subject. The movable unit 40 is fixed to a transmission and reception head 32 of the transmission and reception unit 30 and moves with the movement of the acoustic radiation surface 31.

The pressure signal detection unit 50 includes, for example, a pressure sensor 51 and a compression spring 52. The pressure sensor 51 detects a pressure applied to the compression spring 52 as a pressure signal corresponding to an amount of movement of the movable unit 40. The compression spring 52 is a spring interposed between the pressure sensor 51 and the lever unit 60. The compression spring 52 pushes the pressure sensor 51 and the lever unit 60 in directions in which they separate from each other. The compression spring 52 is pressed by the lever unit 60 moving toward the pressure sensor 51. The pressure sensor 51 detects the pressure when the compression spring 52 is pressed. The compression spring 52 is, for example, a coil spring. The compression spring 52 is an example of a compression spring member.

The lever unit 60 includes, for example, an action rod 61, an actuation rod 62, and a support member 63. The action rod 61 has an elongated rod shape. A tip (point of action) of the action rod 61 is in contact with the compression spring 52, and the support member 63 is provided at a rear end (fulcrum) thereof. The action rod 61 is disposed to roughly follow the acoustic radiation surface 31.

The actuation rod 62 is provided at a midway position (point of force) of the action rod 61 in a longitudinal direction thereof. The actuation rod 62 has a short rod shape and is disposed in a direction in which it intersects the action rod 61, for example, in a direction substantially perpendicular thereto. One end of the actuation rod 62 is in contact with the action rod 61, and the other end is connected to the movable unit 40. The actuation rod 62 moves with the movement of the movable unit 40.

The support member 63 is attached to the probe body 20. The action rod 61 is swingable with the support member 63 as its swing center. The action rod 61 is pushed in the direction of the transmission and reception unit 30 by the compression spring 52. Since the action rod 61 is thus pushed, the actuation rod 62 is in a state in which it is pressed against the movable unit 40.

When the acoustic radiation surface 31 is pressed against the subject, the pressure applied to the acoustic radiation surface 31 provided in the transmission and reception unit 30 is transmitted to the movable unit 40, and the movable unit 40 moves. When the movable unit 40 moves, a pressing force of the movable unit 40 causes the actuation rod 62 to move in a direction away from the transmission and reception unit 30. As the actuation rod 62 moves, the action rod 61 swings around the support member 63, and the rear end of the action rod 61 presses the compression spring 52.

The action rod 61 is connected to the actuation rod 62 at the midway position of the action rod 61 in the longitudinal direction, with the tip of the action rod 61 serving as the point of action and the rear end as the fulcrum. For this reason, an amount of movement of the tip of the action rod 61 is greater than an amount of movement of the actuation rod 62, and the lever unit 60 amplifies the amount of movement of the movable unit 40. The lever unit 60 is an example of an amplification unit.

The actuation rod 62 is in contact with the action rod 61 at a position closer to the support member 63 than a center of the action rod 61 in the longitudinal direction. For this reason, the lever unit 60 amplifies the amount of movement of the movable unit 40 to a greater extent, for example, by twice or more. The actuation rod 62 may be in contact with at any position on the action rod 61 in the longitudinal direction.

A gap P is formed between the probe body 20 and the transmission and reception unit 30 (transmission and reception head 32). Due to the formation of the gap P, the movement of the acoustic radiation surface 31 (transmission and reception unit 30) relative to the probe body 20 gripped by the operator is not hindered. The gap P is filled with a sealant 70. The sealant is made of, for example, silicone having high chemical resistance. The sealant 70 is circumferentially entirely made of silicone that fills the gap P around the entire circumference of the probe body 20 and the transmission and reception unit 30. Since the sealant 70 fills the gap P, intrusion of dust and the like into the probe body 20 is inhibited.

The display 80 displays various types of information. For example, the display 80 displays medical images (ultrasonic images) generated by the ultrasonic image processing device 100, graphical user interface (GUI) images for receiving various operations performed by a user, and the like. The ultrasonic images may be two-dimensional ultrasonic images or three-dimensional ultrasonic images.

The display 80 is, for example, a liquid crystal display, a cathode ray tube (CRT), an organic electroluminescence (EL) display, or the like. The display 80 may be a desktop type, or a display device (for example, a tablet terminal) capable of wireless communication with a main body of the ultrasonic image processing device 100.

The input interface 90 receives various input operations performed by the user and outputs electrical signals indicating the content of the received input operations to the ultrasonic image processing device 100. For example, the input interface 90 is realized by a mouse, a keyboard, a touch panel, a drag ball, switches, buttons, a joystick, a camera, an infrared sensor, a microphone, or the like. The input interface 90 may be provided in a housing. Also, the input interface 90 may be realized by a display device (for example, a tablet terminal) capable of wireless communication with the main body of the ultrasonic image processing device 100.

Also, in the present specification, the input interface is not limited to one having physical operation components such as a mouse and a keyboard. Examples of the input interface include, for example, an electrical signal processing circuit that receives an electrical signal corresponding to an input operation from an external input device provided separately from the device and outputs this electrical signal to a control circuit.

The ultrasonic image processing device 100 includes, for example, a transmission and reception circuit 110, a control circuit 120, a memory 130, and an image processing circuit 140. The transmission and reception circuit 110, the control circuit 120, the memory 130, and the image processing circuit 140 are connected to each other via a bus so that they can communicate with each other.

The transmission and reception circuit 110 includes, for example, a drive circuit that vibrates the transducers in the transmission and reception unit 30 of the ultrasonic probe 10, and the like. The transmission and reception circuit 110 outputs drive signals to the ultrasonic probe 10 via the cable L depending on transmission and reception conditions transmitted by the control circuit 120 and drives the plurality of transducers. The drive signals output by the transmission and reception circuit 110 include information for identifying the transducers that output ultrasound. In the ultrasonic probe 10, the transducers identified by the drive signal are driven.

The transmission and reception circuit 110 receives and acquires an acoustic reflection signal output by the ultrasonic probe 10. The transmission and reception circuit 110 converts the acquired acoustic reflection signal into a digital acoustic reflection signal, which is a digital signal. The transmission and reception circuit 110 outputs the converted digital acoustic reflection signal to the control circuit 120.

The control circuit 120 controls overall processing of the ultrasonic diagnostic device 1. The control circuit 120 is realized, for example, by a hardware processor (computer) executing a program (software) stored in the memory 130. The hardware processor indicates, for example, circuitry including a central processing unit (CPU), a graphics processing unit (GPU), an application specific integrated circuit (ASIC), a programmable logic device (for example, a simple programmable logic device (SPLD) or a complex programmable logic device (CPLD), a field programmable gate array (FPGA)), or the like. Instead of storing a program in the memory 130, the program may be configured to be directly built into a circuit of the hardware processor.

In this case, the hardware processor realizes functions by reading and executing the program built into the circuit. The hardware processor is not limited to being configured as a single circuit, and may be configured as a single hardware processor by combining a plurality of independent circuits to realize each function. Also, a plurality of constituent elements may be integrated into a single hardware processor to realize each function. Each constituent element included in the image processing circuit 140 may be distributed and realized by a plurality of pieces of hardware.

Specifically, the control circuit 120 controls the transmission and reception circuit 110 on the basis of various setting requests input via the input interface 90, and various control programs and various types of data read from the memory 130. The control circuit 120 further performs processing for generating sound images, various types of image processing for ultrasonic images, and the like.

The control circuit 120 generates an image of a captured cross-section of the subject on the basis of the digital acoustic reflection signal output by the transmission and reception circuit 110. The captured cross-section is determined depending on movement of the transmission and reception unit 30 in the ultrasonic probe 10. The captured cross-section is assumed to be, for example, a plane perpendicular to a plane that includes the direction in which the ultrasonic probe 10 moves (a plane assumed to be a surface of the subject) and that follows the direction in which an opening in the transmission and reception unit 30 moves.

The memory 130 is realized by, for example, a semiconductor memory element such as a random access memory (RAM) and a flash memory, a hard disk, an optical disk, or the like. Data such as a program for driving the transmission and reception circuit 110 is stored. Instead of (or in addition to) the memory 130, the data may be stored in an external memory that is external to the ultrasonic image processing device 100 or that can communicate with the ultrasonic image processing device 100. The memory 130 does not have to be built into the ultrasonic image processing device 100 as long as the ultrasonic image processing device 100 can access it over a network.

In the ultrasonic probe 10 of the first embodiment, when the pressure sensor 51 detects a pressure signal corresponding to the amount of movement of the movable unit 40, which moves due to the pressure applied to the acoustic radiation surface 31, the lever unit 60 amplifies the amount of movement of the movable unit 40. For this reason, even if the amount of movement of the movable unit 40 is small, a large pressure can be applied to the pressure sensor 51, and thus a spring constant of the compression spring 52 can be kept small. Accordingly, it is possible to inhibit enlargement of a size of the compression spring 52, and therefore inhibit enlargement of a size of the ultrasonic probe 10.

Figure 3:
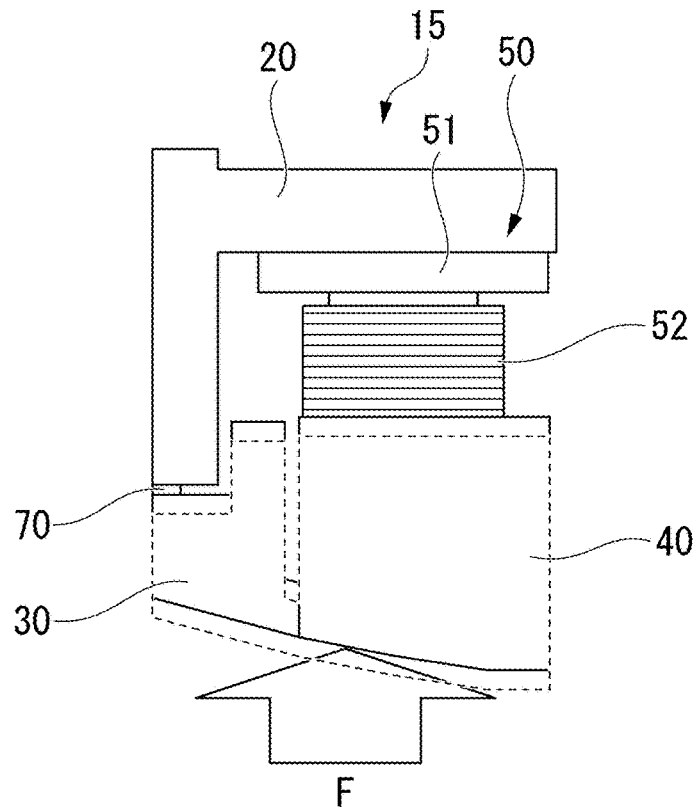
FIG. 3 is a cross-sectional view of main parts of an ultrasonic probe in the related art.

Next, the compression spring 52 and the sealant 70 used in the ultrasonic probe 10 will be described in relation to the related art. FIG. 3 is a cross-sectional view of main parts of an ultrasonic probe 15 in the related art. As compared to the ultrasonic probe 10 of the first embodiment, the ultrasonic probe 15 in the related art does not have the lever unit 60.

In addition, although the ultrasonic probe 15 in the related art also includes the compression spring 52 interposed between the movable unit 40 and the pressure sensor 51, the compression spring 52 in the ultrasonic probe 15 has a larger spring constant than the compression spring 52 in the ultrasonic probe 10. For this reason, the compression spring 52 in the ultrasonic probe 15 is larger than the compression spring 52 in the ultrasonic probe 10.

In the ultrasonic probes 10 and 15, the sealant 70 is filled around the entire circumference between the probe body 20 and the transmission and reception unit 30. If the sealant 70 is filled around the entire circumference of the gap between the probe body 20 and the transmission and reception unit 30 and the gap is filled, the sealant 70 will hinder the movement of the acoustic radiation surface 31 (the transmission and reception unit 30), making it difficult for the acoustic radiation surface 31 to move.

In addition, if the pressure applied to the acoustic radiation surface 31 is large and an excessive force is applied to the sealant 70, a material of the sealant 70 will deteriorate, causing damage and peeling. Further, the force applied to the acoustic radiation surface 31 is also transmitted directly to the subject. For example, if the acoustic radiation surface 31 is pressed against subjects and a force of several tens of [N] is applied to the subjects, some subjects may feel pain.

A case in which the ultrasonic probe 15 in the related art is to tolerate an external force of up to 70 [N] is conceivable. In this case, for example, when a movable distance $\Delta l$ of the acoustic radiation surface 31 is set to $\Delta l=0.1$ [mm], a spring constant k1 of the sealant 70 is set to k1=300 [N/mm], and the maximum external force F is set to F=70 [N], the maximum spring constant k2 of the compression spring 52 is required to be set to 400 [N/mm] according to the following (1).

$$k1 * \Delta l + k2 * \Delta l \leq F \quad (1)$$

Since the compression spring 52 having the maximum spring constant k2 of 400 [N/mm] requires a diameter of 25 mm or more if it is made of, for example, oil-tempered wire, it will become a very large and thick spring. If such a large and thick spring is housed inside an ultrasonic probe, it will lead to an increase in size of a probe shape, which may impair ergonomics.

In contrast, in the ultrasonic probe 10 of the first embodiment, the lever unit 60 is interposed between the movable unit 40 and the compression spring 52. Here, when a leverage ratio Y of the lever unit 60 is taken into consideration, the following expression (2) is satisfied.

$$k1 * \Delta l + k2 * \Delta l * Y \leq F \quad (2)$$

When the movable distance $\Delta l = 0.1$ [mm] of the acoustic radiation surface 31, the spring constant k1=300 [N/mm] of the sealant 70, and the maximum external force F=70 [N] are substituted into the above expression (2), the maximum spring constant k2 of the compression spring 52 can be expressed by the following expression (3).

$$k2 \leq 400/Y \quad (3)$$

Thus, in the ultrasonic probe 10 of the first embodiment, the lever unit 60 is interposed between the movable unit 40 and the compression spring 52, and thus the compression spring 52 can be made compact as compared to the ultrasonic probe 15 in the related art. Accordingly, it is possible to inhibit enlargement of the size of the ultrasonic probe 10.

Second Embodiment

Figure 4:
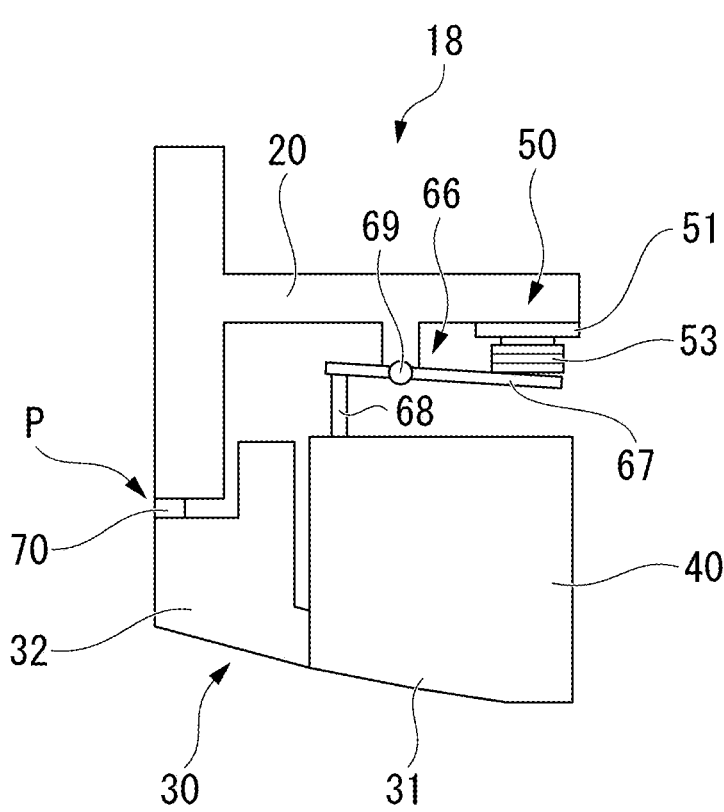
FIG. 4 is a cross-sectional view of main parts of an ultrasonic probe according to a second embodiment.

Next, a second embodiment will be described. FIG. 4 is a cross-sectional view of main parts of an ultrasonic probe 18 of the second embodiment. The ultrasonic probe 18 of the second embodiment is different from the ultrasonic probe 10 of the first embodiment mainly in that it includes a lever unit 66 instead of the lever unit 60 of the ultrasonic probe 10 of the first embodiment, and a tension spring 53 instead of the compression spring 52. The tension spring 53 is an example of a tension spring member. The spring member used as the compression spring 52 of the first embodiment and the tension spring 53 of the second embodiment is a coil spring, but may be a spring other than a coil spring, such as a leaf spring, a disc spring, or a spiral spring.

The tension spring 53 in the ultrasonic probe 18 is a spring interposed between the pressure sensor 51 and the lever unit 66. The tension spring 53 is attached to the pressure sensor 51 and the lever unit 66 and pulls the pressure sensor 51 and the lever unit 66 in directions in which they attract each other. The tension spring 53 is stretched by the lever unit 66, which moves in a direction away from the pressure sensor 51. The pressure sensor 51 detects a pressure that is released when the tension spring 53 is stretched.

The lever unit 66 in the ultrasonic probe 18 includes, for example, an action rod 67, an actuation rod 68, and a support member 69. The action rod 67 has an elongated rod shape. A tip (point of action) of the action rod 67 comes into contact with the compression spring 52, and one end of the actuation rod 68 is connected to a rear end (point of force) thereof. The action rod 67 is disposed to roughly follow the acoustic radiation surface 31.

The actuation rod 68 has a short rod shape and is disposed in a direction intersecting the action rod 67, for example, in a direction substantially perpendicular to the action rod 67. One end of the actuation rod 68 is in contact with the action rod 67, and the other end is connected to the movable unit 40. The actuation rod 68 moves with the movement of the movable unit 40.

The support member 69 is provided at a midway position (fulcrum) of the action rod 67 in a longitudinal direction thereof. The support member 69 is attached to the probe body 20. The action rod 67 is swingable with the support member 69 as its swing center. The action rod 67 is pulled in the direction of the pressure sensor 51 by the tension spring 53. Since the support member 69 is located at the midway position of the action rod 67 and the actuation rod 68 is connected to the rear end of the action rod 67, the tip of the action rod 67 is thus pushed, and the actuation rod 68 is in a state in which it is pressed against the movable unit 40.

When the acoustic radiation surface 31 moves relative to the probe body 20, the pressure applied to the acoustic radiation surface 31 is transmitted to the movable unit 40, causing the movable unit 40 to move. When the movable unit 40 moves, the pressing force of the movable unit 40 causes the actuation rod 68 to move in a direction away from the transmission and reception unit 30. As the actuation rod 68 moves, the action rod 67 swings around the support member 69, and the tip of the action rod 67 stretches the tension spring 53.

The action rod 67 is connected to the actuation rod 68 at a rear end of the action rod 67, with the tip of the action rod 67 serving as the point of action and its midway point in the longitudinal direction serving as the fulcrum. A length from the fulcrum to the point of action in the action rod 67 is longer than a length from the fulcrum to the point of force. For this reason, an amount of movement of the tip of the action rod 67 is larger than an amount of movement of the actuation rod 68, and the lever unit 60 amplifies the amount of movement of the movable unit 40.

The ultrasonic probe 18 of the second embodiment has the same axle operation and effect as the ultrasonic probe 10 of the first embodiment. Further, in the ultrasonic probe 18 of the second embodiment, the pressure detected by the pressure sensor 51 is the pressure released when the tension spring 53 is stretched. For this reason, a pressure load applied to the pressure sensor 51 can be reduced at all times, and thus it is possible to inhibit wear of the pressure sensor 51.

In the above embodiment, the lever units 60 and 66 are used as amplification units that amplify the amount of movement of the movable unit 40, but the amplification unit may have a configuration other than the lever units. The amplification unit may be, for example, a gear mechanism formed by combining gears having different diameters, or a diaphragm including liquid chambers having different volumes.

According to at least one embodiment described above, the ultrasonic probe includes the transmission and reception unit that includes a plurality of transducers, transmits transmission acoustic signals generated by the transducers, and receives reflection acoustic signals of the transmission acoustic signals, the movable unit that includes the acoustic radiation surface provided on a surface of the transmission and reception unit and moves due to a pressure applied to the acoustic radiation surface pressed against an object, the pressure signal detection unit configured to detect a pressure signal corresponding to an amount of movement of the movable unit, and the amplification unit configured to amplify the amount of movement of the movable unit, and thus it is possible to inhibit enlargement of a size of the ultrasonic probe.

Although several embodiments have been described, these embodiments are presented as examples and are not intended to limit the scope of the invention. These embodiments can be implemented in various other forms, and various omissions, substitutions, and modifications can be made without departing from the spirit of the invention. These embodiments and their modifications are included in the invention and its equivalents as set forth in the claims, as included within the scope and the gist of the invention.

What is claimed is:

1. An ultrasonic probe, comprising:
a transmission and reception unit that includes a plurality of transducers, transmits transmission acoustic signals generated by the transducers, and receives reflection acoustic signals of the transmission acoustic signals;
a movable unit that includes an acoustic radiation surface provided on a surface of the transmission and reception unit and moves due to a pressure applied to the acoustic radiation surface pressed against an object;
a pressure signal detection unit configured to detect a pressure signal corresponding to an amount of movement of the movable unit; and
a lever unit configured to amplify the amount of movement of the movable unit; and
a spring member interposed between the pressure signal detection unit and the movable unit,
wherein the lever unit is interposed between the movable unit and the spring member, and includes an action rod, an actuation rod, and a support member.

2. The ultrasonic probe according to claim 1, wherein the lever unit is configured to amplify an amount of movement of the acoustic radiation surface.

3. The ultrasonic probe according to claim 2, wherein the pressure signal detection unit includes a pressure sensor configured to detect the pressure signal.

4. The ultrasonic probe according to claim 3, wherein the movable unit applies a pressure to the pressure sensor by the movement of the movable unit, and
the spring member is a compression spring member.

5. The ultrasonic probe according to claim 3, wherein the movable unit releases a pressure applied to the pressure sensor by the movement of the movable unit, and
the spring member is a tension spring member.

6. The ultrasonic probe according to claim 3, wherein a maximum spring constant of the spring member is determined on a basis of a moving distance of the acoustic radiation surface, a leverage ratio of the lever unit, and the pressure.

7. The ultrasonic probe according to claim 6, wherein the maximum spring constant of the spring member is determined to be equal to or smaller than a value obtained by dividing 400 by the leverage ratio under a condition that the moving distance of the acoustic radiation surface is 0.1 [mm] and the pressure is 70 [N].

8. The ultrasonic probe according to claim 1, further comprising:
a probe body to which the pressure signal detection unit is attached,
wherein a gap between the probe body and the transmission and reception unit is filled with a silicone sealant around the entire circumference thereof.

9. The ultrasonic probe according to claim 1,
wherein the action rod has an elongated rod shape,
wherein a tip of the action rod is in contact with the spring member, and
wherein the support member is provided at a rear end of the action rod.

10. The ultrasonic probe according to claim 1,
wherein the actuation rod is provided at a midway position of the action rod in a longitudinal direction thereof,
wherein the actuation rod has a short rod shape and is disposed in a direction in which the actuation rod intersects the action rod in a direction substantially perpendicular thereto,
wherein one end of the actuation rod is in contact with the action rod, and another end is connected to the movable unit, and
wherein the actuation rod is configured to move with a movement of the movable unit.

11. The ultrasonic probe according to claim 1, further comprising a probe body,
wherein the support member is attached to the probe body,
the action rod is swingable with the support member as a swing center,
the action rod is pushed in a direction of the transmission and reception unit by the spring member, and
when the action rod is thus pushed, the actuation rod is configured to be in a state in which the actuation rod is pressed against the movable unit.

* * * * *